(12) United States Patent
Baumgartner et al.

(10) Patent No.: US 7,597,713 B2
(45) Date of Patent: Oct. 6, 2009

(54) INTERVERTEBRAL IMPLANT COMPRISING A THREE-PART ARTICULATION

(75) Inventors: Daniel Baumgartner, Oensingen (CH); Adrian Burri, Brig (CH); Claude Mathieu, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 825 days.

(21) Appl. No.: 10/526,293

(22) PCT Filed: Sep. 2, 2002

(86) PCT No.: PCT/CH02/00476

§ 371 (c)(1),
(2), (4) Date: Mar. 1, 2005

(87) PCT Pub. No.: WO2004/019828

PCT Pub. Date: Mar. 11, 2004

(65) Prior Publication Data

US 2006/0036326 A1    Feb. 16, 2006

(51) Int. Cl.
*A61F 2/44* (2006.01)
(52) U.S. Cl. ............... 623/17.15; 623/17.16; 623/20.18; 623/21.18
(58) Field of Classification Search ............... 623/17.14, 623/17.15, 18.11, 20.18, 20.29, 20.33, 21.18, 623/17.16
See application file for complete search history.

(56) References Cited

U.S. PATENT DOCUMENTS

| | | | |
|---|---|---|---|
| 4,759,766 A * | 7/1988 | Buettner-Janz et al. | .. 623/17.15 |
| 5,534,030 A * | 7/1996 | Navarro et al. | ........... 623/17.15 |
| 5,879,387 A * | 3/1999 | Jones et al. | ............... 623/18.11 |
| 6,019,792 A | 2/2000 | Cauthen | |
| 6,179,874 B1 | 1/2001 | Cauthen | |
| 6,440,168 B1 | 8/2002 | Cauthen | |

FOREIGN PATENT DOCUMENTS

DE    3023 353 C2    4/1982

* cited by examiner

*Primary Examiner*—Corrine M McDermott
*Assistant Examiner*—Christopher D Prone
(74) *Attorney, Agent, or Firm*—Stroock & Stroock & Lavan LLP

(57) ABSTRACT

An intervertebral implant including: a central axis, upper and lower terminal parts and a convex joint element. Each of the terminal parts come to rest against the end surfaces of two adjacent vertebras and opposite first and second concave inner surfaces, respectively. The convex joint element is situated between the terminal parts and rests in a sliding manner against the first and second concave inner surfaces of the two terminal parts. The, first concave surface is a partial surface of a first rotationally symmetrical external surface about the axis of rotation transverse to the central axis. The second concave inner surface of a second rotationally symmetrical conical external surface about the axis of rotation transverse to the central axis.

12 Claims, 5 Drawing Sheets

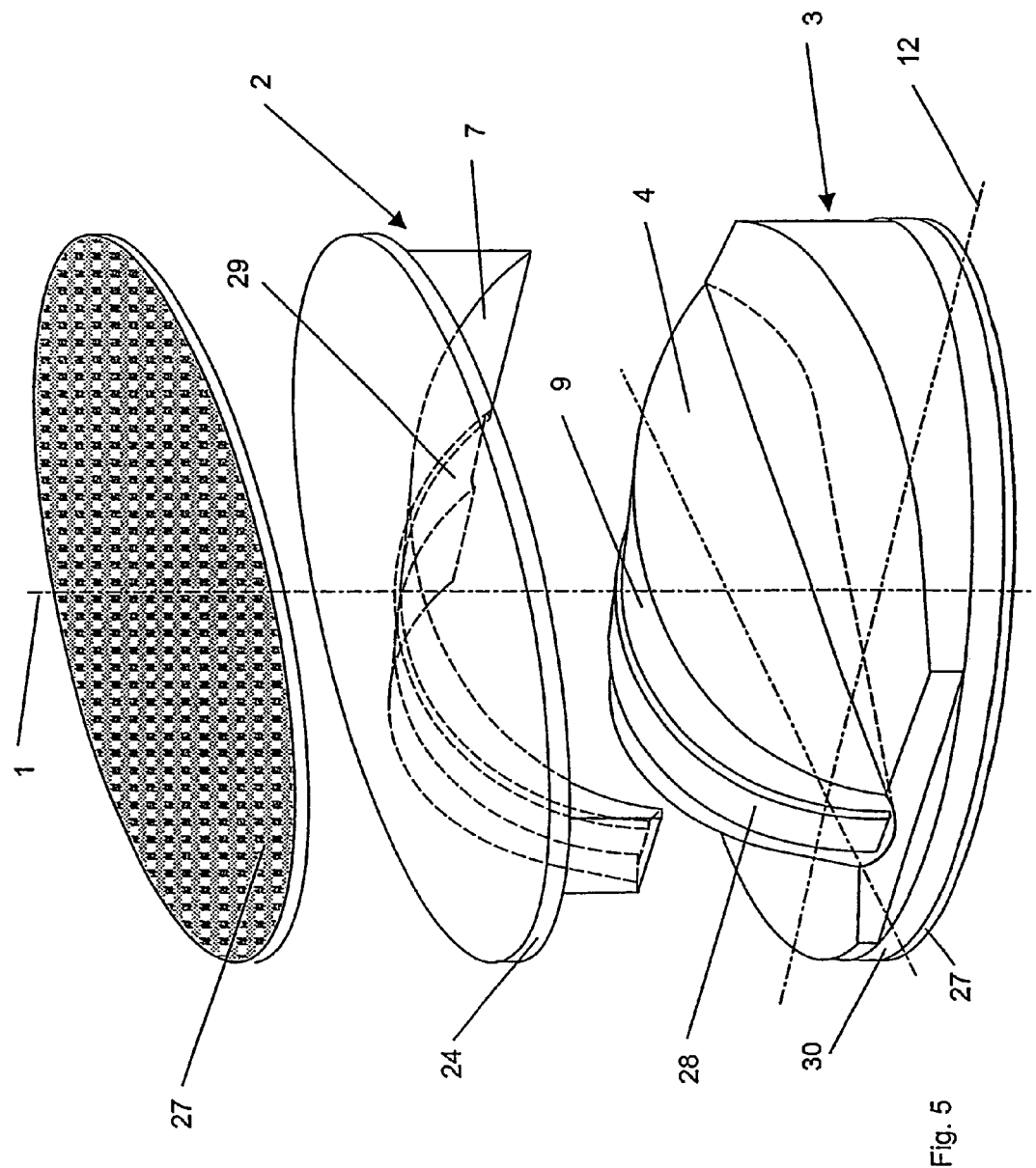

INTERVERTEBRAL IMPLANT COMPRISING A THREE-PART ARTICULATION

Figure 1:
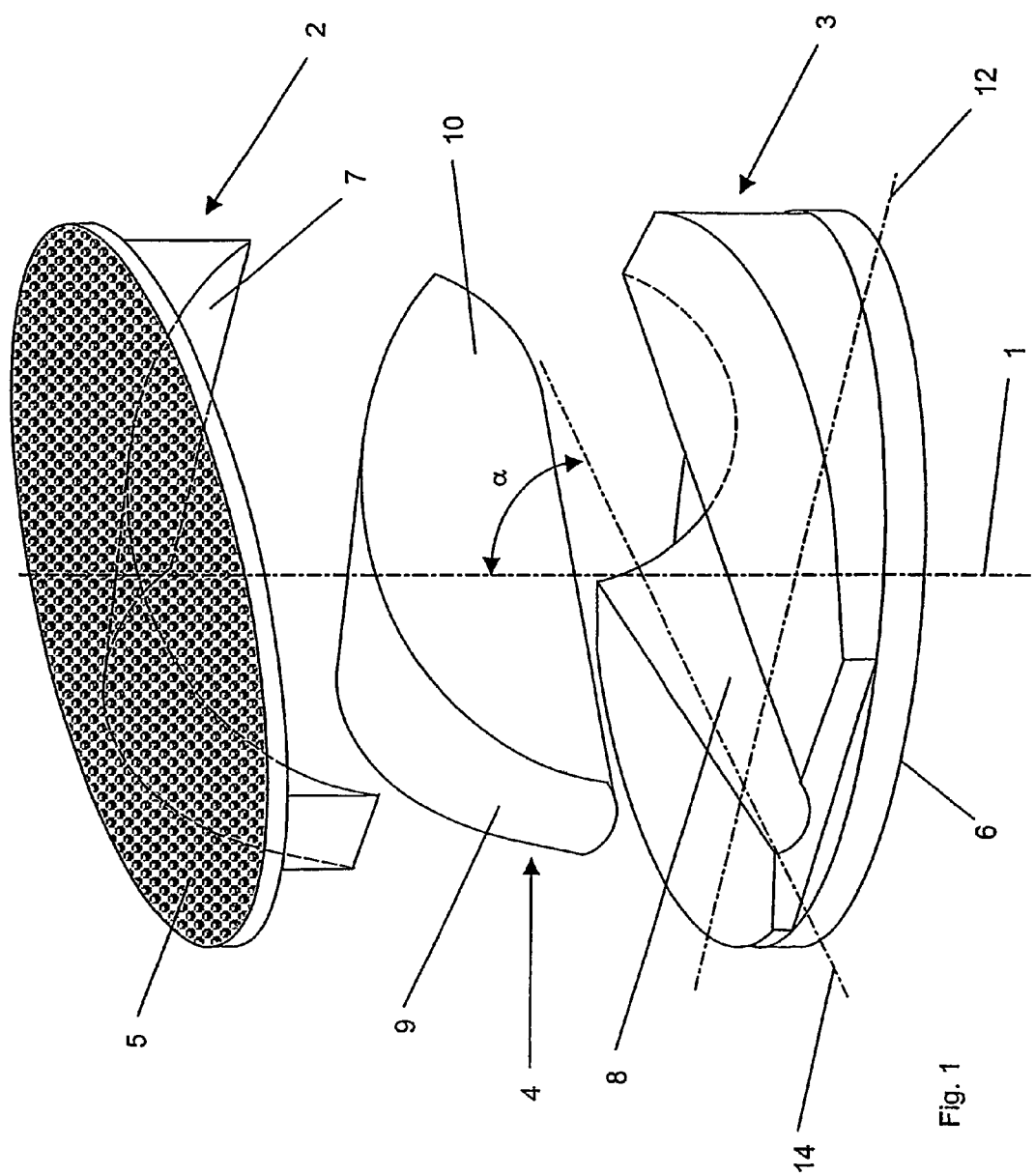

The present invention relates to an intervertebral implant defined in the preamble of claim 1.

Upon removal of a natural, damaged intervertebral disk or a damaged nucleus of an intervertebral disk, implants or prostheses are inserted into the intervertebral space between two adjacent vertebras. The objective is also to restore the most natural conditions possible, that is, in particular to restore the original intervertebral disk height and thence the original spacing between the two adjacent vertebras. Moreover relative displacements between the adjacent vertebras should be possible in a natural way in the most hamper-free way possible. Preservation of displaceability during forward/ backward motions, that is when the vertebras shall be flexed or extended, also when the vertebras shall be bent, within natural boundaries, is then essential. Again the mutual rotations of the adjacent vertebras also should be possible within natural bounds.

A vertebral disk endosprosthesis of this kind is known from the BÜTTNER European patent document 0 176 728. This known vertebral disk endoprosthesis substantially consists of two symmetrical, concave sealing plates of which the external surfaces each may be made to rest against one of the end plates of the adjacent vertebras, and of a convex spacer configured between the mutually opposite concave sides of the terminal plates. This known vertebral disk endoprosthesis incurs the following drawbacks:

the axes of rotation relating to bending/stretching and also to laterally bending the adjacent vertebras by means of the joint-like connection are defined only within a given range and do not coincide with natural physiological conditions, the play in displacement is the same laterally and ventrally/ dorsally because the prosthesis exhibits symmetry of rotation when using the Pe-inlay. The natural averages of motional play, that is the rotation of the terminal plates about axes or the rotation transverse to the longitudinal axis of the spinal column are 10°, 5° for stretching and 7° for lateral motions;

the prosthesis does not include displacement restricting means regarding relative rotation of the terminal plates about an axis of rotation which is coaxial with or parallel to the longitudinal axis of the spinal column (vertebra twisting), and the prosthesis offers only minor damping against applied shocks.

The objective of the present invention is palliation. Its goal is to create an intervertebral implant offering a particular defined axis of rotation for the lateral displacement of the spinal column, and for the bending and stretching of the adjacent vertebras, said axes of rotation crossing each other and subtending different angles with the central axis.

The present invention solves the stated problem by means of an intervertebral implant and in particular by an intervertebral implant exhibiting the features of claim 1.

The intervertebral implant of the present invention comprises a central axis substantially parallel to or coaxial with the spinal column's longitudinal axis, further a lower and an upper terminal part, each comprising an outermost surface transverse to the central axis and each comprising two mutually opposite surfaces, each surface being concave, further a joint element positioned in sliding manner at the concave inner surfaces. The outermost surfaces of the terminal parts each may be made to rest against one of the two end surfaces of two adjacent vertebras. The first concave inner surface configured at the upper terminal part is designed in the form of a first lateral surface which is rotationally symmetric relative to the axis of rotation and runs transversely to the central axis. The second inner surface configured at the lower terminal part is designed as a partial surface of a conical outer surface which is rotationally symmetric to the axis of rotation that is transverse to the central axis, as a result of which the second axis of rotation coincides with the cone's longitudinal axis.

It is assumed herebelow that the lower terminal part is affixed in position and in that the joint element as well as the upper terminal part are displaceable. Hence the second axis of rotation—which is determined by the concave second inner surface that is rotationally symmetric relative to the second axis of rotation, also is affixed in position, whereas the first axis of rotation, which is determined by the first concave inner surface that is rotationally symmetric relative to the first axis of rotation, and hence is fixed in position relative to the upper terminal part, together with the joint element and the upper terminal part shall be rotated about the second axis of rotation when the joint element together with the upper terminal part will be rotated about the second axis of rotation. Herebelow, the central axis also is assumed stationary relative to the lower terminal part.

In the preferred embodiment mode of the intervertebral implant of the present invention, the said axes of rotation will cross one another. Preferably these axes of rotation intersect the central axis.

Essentially the advantages offered by the present invention are deemed to be that its intervertebral implant enables the two axes of rotation to be configured in two different planes transverse to the central axis. As a result, the axis of rotation of central spinal column bending and the central axis for spinal column bending/stretching may be offset from each other and may be configured within non-parallel planes. This design allows precisely imitating the positions of the natural axes of rotation, and consequently the bio-mechanics of the two adjacent vertebras may substantially approximate the healthy condition of the spinal column, or even this healthy condition may be restored completely. Because the physiological axes of rotation are taken into account, no increased torques are applied to the ligaments, sinews and muscles while retaining the distances between center of rotation and force application point.

In another embodiment mode of the intervertebral implant of the present invention, the slide surfaces of the joint element are not complementary to the concave inner surfaces of the terminal parts, resulting thereby in a point-like or linear contact between the slide surfaces and the concave inner surfaces of the two terminal parts. Illustratively a linear contact may be attained in that the slide surfaces exhibit a lesser radius of curvature at the joint element than do the adjoining concave inner surfaces of the terminal parts. Illustratively a point-like contact between the first concave inner surface and the adjoining joint element at the slide surface may be attained by a spherical, ellipsoid of rotation or barrel-like design of the joint element's slide surface and, depending on the embodiment mode, also of the first concave inner surface.

In yet another embodiment mode of the intervertebral implant of the present invention, the joint element comprises at least one convex slide surface which is transverse to the central axis and complementary to the concave inner surface of the adjoining terminal part. Preferably both slide surfaces are complementary to the terminal parts' convex inner surfaces, the first slide surface being complementary to the concave inner surface of the upper terminal part and the second slide surface being complementary to the concave inner surface of the lower terminal part. In this embodiment mode, the first concave inner surface and the first slide surface are designed as partial surfaces of a first external surface exhibiting symmetry of rotation and transverse to the central axis and they constitute the slide surfaces of a first joint rotatable about the first axis of rotation. The second concave inner surface and the second slide surface are designed as partial surfaces of an external, conical surface constituting the slide surfaces of a second joint rotatable about a second axis of rotation, said second axis of rotation corresponding to the cone's longitudinal axis.

As regards a further embodiment mode of the intervertebral implant of the present invention, the two axes of rotation are configured in a manner that the second axis of rotation is contained in a plane also containing the central axis and being traversed by the first axis of rotation. This feature offers the advantage that the first axis of rotation, and thereby the axis of rotation of spinal column bending and stretching shall be perpendicular to the vertebral implant's central axis when the joint element is not rotated about the second axis of rotation. The second axis of rotation is used to laterally bend the spinal column and may include an angle $\alpha$ to the central axis matching natural displacement. Preferably this angle $\alpha$ is within the range of 60 to 88°. By selecting the angle $\alpha$ and depending on the height of the intervertebral disk, the different lumbar spinal column segments may be imitated physiologically.

In yet another embodiment mode of the intervertebral implant of the present invention, the external surface rotationally symmetrical to the first axis of rotation is a circularly cylindrical external surface. The first convex inner surface at one of the terminal parts as well as the first slide surface at the joint element therefore are designed as partial surfaces of a circularly cylindrical external surface, whereby the first joint is rotatable only relative to the first axis of rotation. As a result, a specific bending/stretching motion is made possible. Moreover separate consideration of this scenario of motion is feasible because the axis of rotation of lateral bending is situated elsewhere.

Instead of the external surface rotationally symmetrical relative to the first axis of rotation being a circularly cylindrical external surface, it may also be in the form of an external conical surface. Further designs of the external surface rotationally symmetrical with respect to the first axis of rotation illustratively are surface portions of an ellipsoid of revolution, a double cone or also another arbitrary body of revolution.

In yet another embodiment mode of the intervertebral implant of the present invention, the first axis of rotation intersects the central axis and as a result, when the spinal column is bent or stretched, the center of rotation of the two vertebras adjoining the intervertebral implant will be situated on the intervertebral implant's central axis. The second axis of rotation of the second joint also intersects the central axis. In this case the two axes of rotation are apart by a minimum distance A. Preferably this distance A is between 0 and 18 mm. This distance A depends on the anatomical particulars of the centers of rotation, for instance on the fact that the axis of rotation of lateral bending drops diagonally in the dorsal direction in the median plane of the human body.

In yet another embodiment mode of the intervertebral implant of the present invention, the outermost surfaces of the terminal parts exhibit a three-dimensional structure, for instance a roughened surface, to enhance the growth of the adjoining vertebras onto the intervertebral implant.

As regards another embodiment mode of the intervertebral implant of the present invention, the three-dimensional structure is replaced by a grid, preferably a titanium grid, again to enhance growth by the vertebra end plates onto the intervertebral implant.

In still another embodiment mode of the intervertebral implant of the present invention, at least one of the terminal parts comprises first and second stops to limit the mutual motions between the terminal parts. These stops serve to limit the relative motion of the terminal parts about the first axis of rotation enabling bending and stretching the adjacent vertebras. Preferably lateral bending of the two vertebras adjoining the intervertebral implant shall be restricted by third stops. These third stops limit the relative rotation between the terminal parts about the second axis of rotation. The stops are designed in a manner to allow maximum stretching between 2 and 15° and maximum lateral bending between ±5° and ±10°.

As regards one embodiment mode of the intervertebral implant of the present invention, one of the terminal parts includes three elements. This terminal part comprises an outermost cover plate, further a joint pan enclosing the concave inner surface and an elastically deforming spacer mounted in-between transversely to the central axis. Inserting said elastically deforming spacer offers the advantage that on one hand compressive motion of the two adjacent vertebras shall be damped and on the other hand that shearing and torsional displacements between the two terminal parts of the intervertebral implant are feasible.

Further advantageous embodiments of the present invention are characterized in the dependent claims.

The invention and further of its developments are elucidated below in the partly schematic drawings of several illustrative embodiments.

Figure 2:
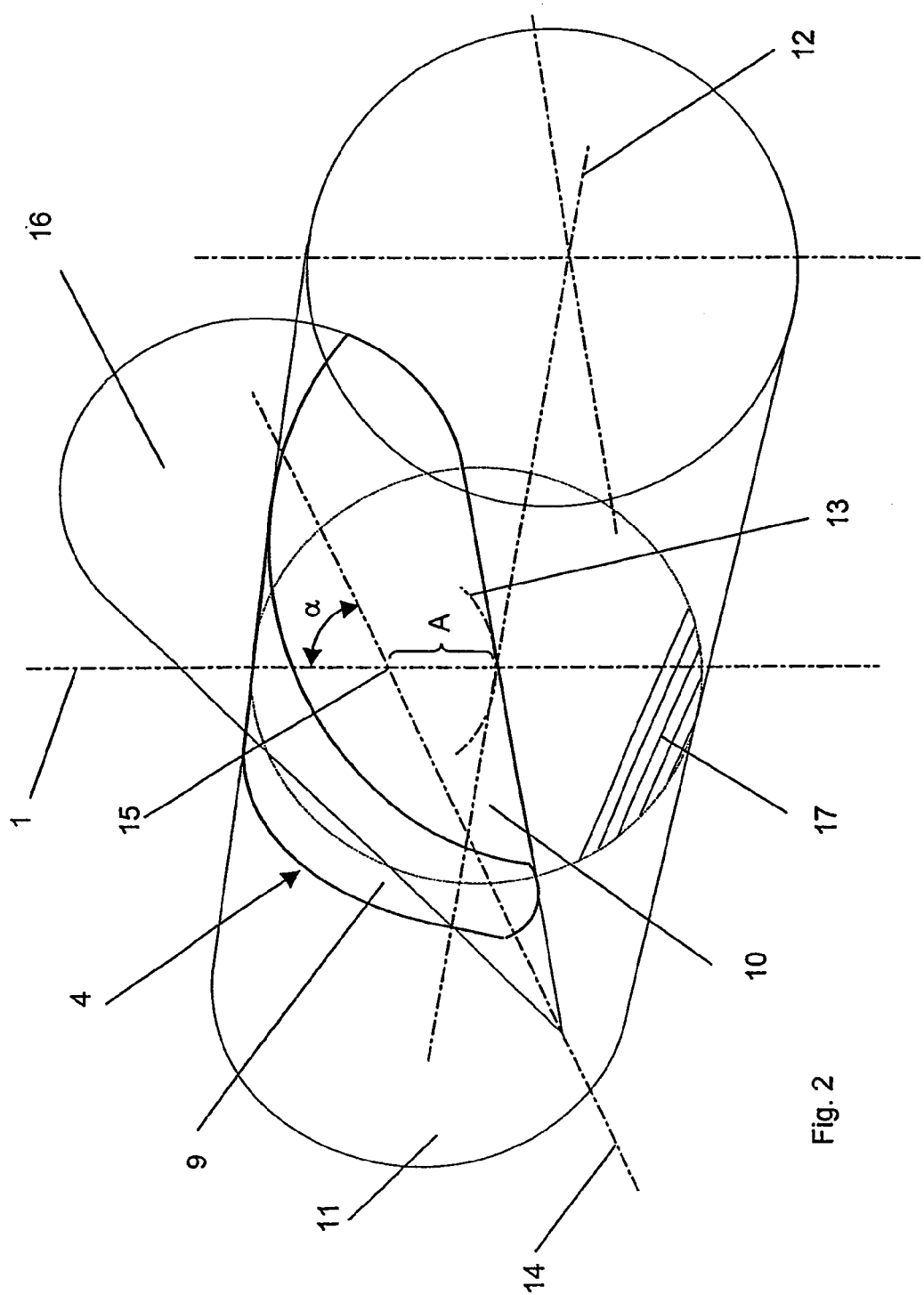
Figure 3:
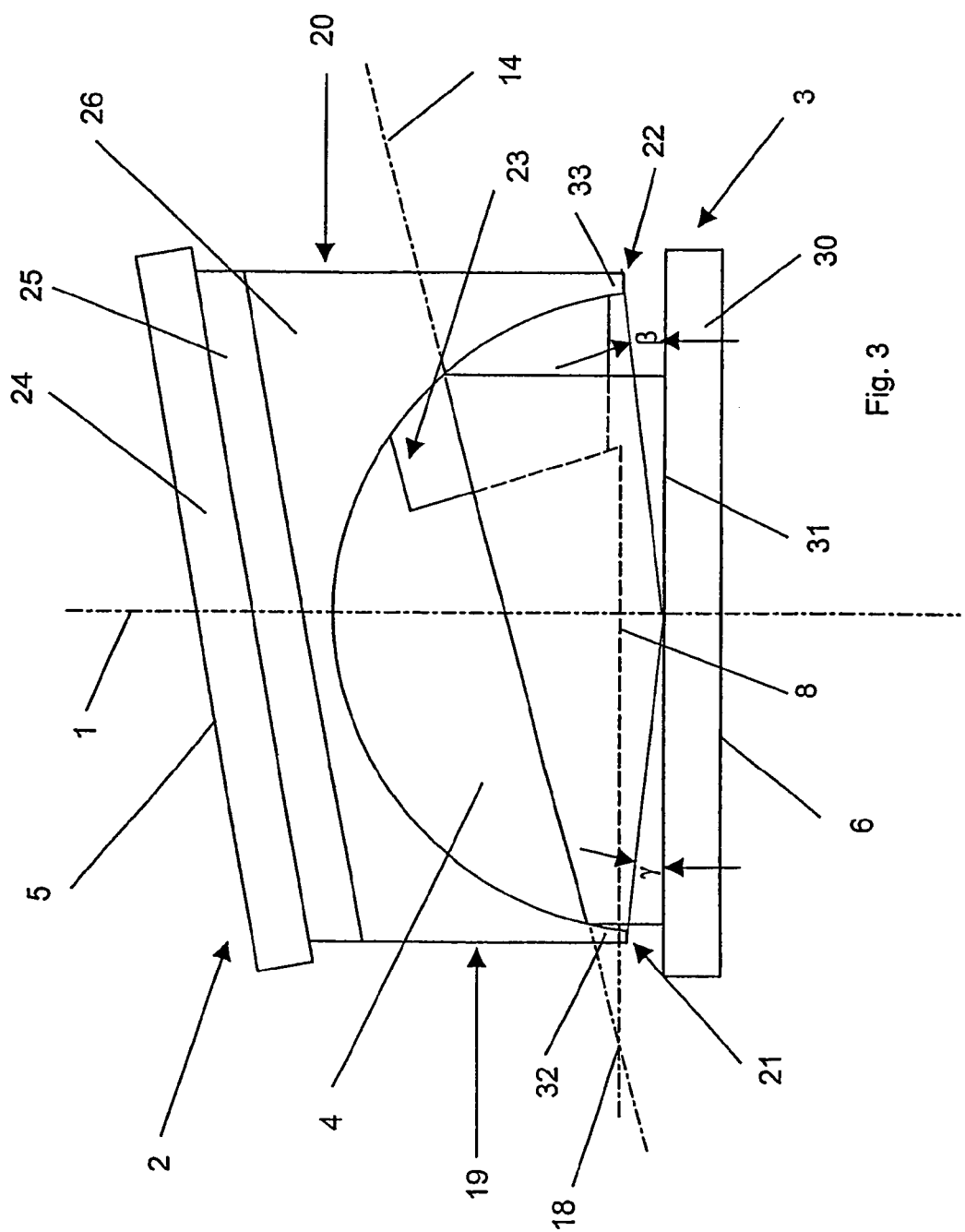
Figure 4:
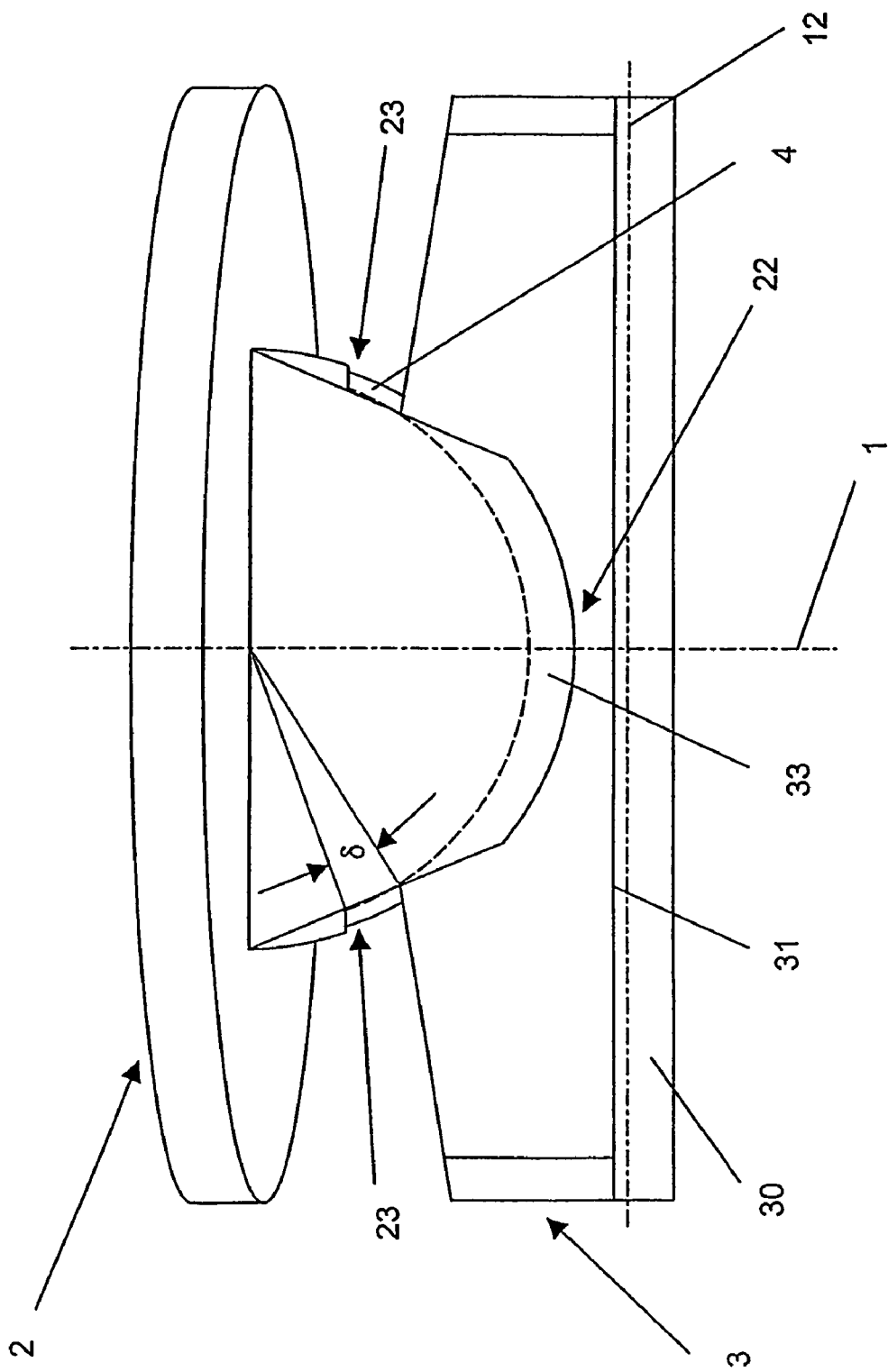

FIG. 1 is an exploded view of an embodiment mode of the intervertebral implant of the invention, FIG. 2 is a perspective view of the joint element with the external surfaces containing the slide surfaces and being rotationally symmetrical to the axes of rotation of the embodiment mode shown in FIG. 1 of the intervertebral implant of the invention, FIG. 3 is a sideview of an embodiment mode of the intervertebral implant of the invention, FIG. 4 is a view from the rear of the embodiment mode shown in FIG. 3 of the intervertebral implant of the invention, and FIG. 5 is an exploded view of another embodiment mode of the intervertebral implant of the invention.

FIG. 1 shows an embodiment mode of the intervertebral implant of the invention comprising an upper and a lower terminal part 2; 3 intersecting the central axis 1 and furthermore a joint element 4 which is situated between the terminal parts 2; 3 and which also intersects the central axis 1. Each terminal part 2; 3 comprises an outermost surface 5; 6 matched to the end plates of the adjoining vertebras and running transversely to the central axis 1, each of said outermost surfaces being displaceable in a manner to come to rest against one of the mutually end surfaces of two adjacent vertebras. The mutually opposite two terminal parts 2; 3 each comprise one concave inner surface 7; 8 whereas the joint element 4 comprises two convex slide surfaces 9; 10 of which the slide surface 9 is complementary to the concave inner surface 7 of the upper terminal part 2 and the other convex slide surface 10 is complementary to the concave inner surface 8 of the lower terminal part 3. The first concave inner surface 7 and the first slide surface 9 complementary thereto constitute the slide surfaces of a first joint rotatable about the first axis of rotation 12 between the joint element 4 and the upper terminal part 2. When the joint element 4 is in its initial position, that is, when it was not rotated about the second axis of rotation 14, the first axis of rotation 12 will be perpendicular to the central axis 1. Rotation of the upper terminal part 2 about the first axis of rotation 12 entails a bending or stretching displacement of the vertebras adjoining the terminal parts 2; 3. The first concave inner surface 7 at the upper terminal part 2 and its complementary first slide surface 9 at the joint element 4 are designed in the embodiment mode presently being discussed of the intervertebral implant of the invention as partial surfaces of a circularly cylindrical outermost surface rotationally symmetrical to the axis of rotation 12. The second concave inner surface 8 and its complementary second slide surface 10 constitute the slide surfaces of a second joint rotatable about a second axis of rotation 14 and situated between the joint element 4 and the lower terminal part 3. This second axis of rotation 14 intersects the central axis 1 at an angle α but does not intersect the axis of rotation 12. As shown in FIG. 2, the second axis of rotation 14 is situated in a plane 17 containing the central axis 1 and is traversed by the first axis of rotation 12. Accordingly rotating the joint element 4 together with the upper terminal part 2 about the second axis of rotation 14 allows laterally bending the two vertebras adjoining the intervertebral implant. FIG. 2 also shows that the external surface 11 rotationally symmetrical about the first axis of rotation 12 is a circularly cylindrical external surface of which the first slide surface 9 constitutes a surface patch. The second slide surface 10 is a surface patch of a second circularly cylindrical external surface 16 which is rotationally symmetrical with respect to the second axis of rotation 14. Moreover the two axes of rotation are a distance A apart. As shown in FIG. 2, as the joint element 4 is rotated about the second axis of rotation, the first axis of rotation 12 moves along an arc 13 of radius A relative to and concentrically with the point of intersection 15 between the central axis 1 and the second axis of rotation 14.

FIG. 3 shows an embodiment mode of the intervertebral implant of the invention that differs from that of FIG. 1 in that the upper terminal part 2 consists of three elements. The upper terminal part 2 comprises in axially outermost manner the upper cover plate 24 containing the outermost surface 5, further a joint pan 26 pointing toward the joint element 4 and an elastically deforming spacer 25 between the joint pan 26 and the cover plate 24. The intervertebral implant moreover comprises a front side 19 pointing toward the cone tip 18, and oppositely a rear side 20. The intervertebral implant is designed in a manner that following implantation, the front side 19 shall be positioned to the rear of the intervertebral space. As a result the second axis of rotation 14 runs from the front to the rear. The rotation of the upper terminal part 2 about the first axis of rotation 12 (FIG. 1) perpendicular to the plane of the Figure is limited by the two stops 21; 22. The first stop 21—which serves to limit a rotation of the two terminal parts 2; 3 relative to each other shortening the front side 19 parallel to the central axis 4 and hence restricting the stretching displacement of the two adjoining vertebras—is mounted at the front side 19 on the upper terminal part 2, whereas the second stop 22 serves to restrict a rotation of the two terminal parts 2; 3 relative to each other, shortening the rear side 20 parallel to the central axis 1, restricting the stretching displacement of the two adjoining vertebras. The first and second stops 21; 22 are constituted by the lower ends 32; 33 respectively situated on the front side 19 and rear side 20 of the upper terminal part 2 that rest against the inner surface 31 facing the joint element 4, of the lower terminal part 3, after the maximum admissible angle of rotation has been reached. FIG. 4 shows that the lower end 33 is rounded off at the rear side 20 (FIG. 3), the center of this rounded segment coinciding with the intersection between the second axis of rotation 14 (FIG. 3) and the rear side 20 of the intervertebral implant, as a result of which the first stop 22—when the upper terminal part 2 is rotated about the second axis of rotation 14 (FIG. 3)—shall come to rest at the same angle of rotation about the first axis of rotation 12 against the inner surface 31 of the base plate 30 of the lower terminal part 3. Furthermore the second slide surface 10 (FIG. 1) is offset at the rear side 20 of the intervertebral implant over part of its periphery and part of its length. The second concave inner surface 8 is similarly offset. The stop 23 ensuing from this offset limits the angle of rotation of the upper terminal part 2 about the second axis of rotation 14, as a result of which the lateral bending of the two vertebras adjoining the intervertebral implant shall be restricted. The stops 21; 22; 23 are designed in a manner to allow bending the adjacent vertebras through an angle β of 10°, stretching by an angle γ=5° and lateral bending by an angle of δ=±7°.

The embodiment mode of the intervertebral implant shown in FIG. 5 differs from the embodiment modes of FIG. 1, 3 or 4 only in that grids 27 are present externally on the cover plate 24 and also on the base plate 30 and in that the first convex slide surface 9 comprises an elevation 28 concentric with the first axis of rotation 12 and that the first concave inner surface 7 contains a recess 29, the elevation 28 being tangentially displaced in the recess 29 when the upper terminal part 2 is rotated relative to the joint element 4. The elevation 28 runs parallel to the first axis of rotation 12 only over a portion of the first slide surface 9 whereas the peripheral extension of the elevation 28 runs over the entire first slide surface 9. The recess 29 in the first concave inner surface 29 is complementary to the said elevation. Other embodiment modes of the intervertebral implant of the invention also allow elevations 28 which are peripherally present only over a portion of the first slide surface 9. The elevation 28 engaging the recess 29 offers the advantages that on one hand lateral stabilization between the first terminal part 2 and the joint element 4 is feasible, shearing motion of the adjoining vertebras parallel to the first axis of rotation 12 being precluded, and on the other hand that it is possible to center the joint element 4 within the intervertebral implant, as a result of which the joint element 4 cannot be displaced parallel to the first axis of rotation relative to the first terminal part 2. Preferably the grids 27 are titanium grids that also may be curved so that optimal growth of the adjoining vertebras onto the intervertebral implant shall be possible.

The invention claimed is:
1. An intervertebral implant having a central axis substantially parallel to or coaxial with an axis of a spinal column, comprising:
an upper and a lower terminal part each fitted with an outermost surface configured transversely to the central axis, said upper terminal part having a first curved inner surface and said lower terminal part having a second curved inner surface, said first and second curved surfaces being opposite one another; and
a joint element configured between the terminal parts and resting in a sliding manner against the curved inner surfaces of the upper and lower terminal parts, the joint element including first and second external convex slide surfaces, the first slide surface contacting the first curved inner surface of the upper terminal part, the second slide surface contacting the second curved inner surface of the lower terminal part, the first curved inner surface and the first slide surface forming a first joint rotatable about a first axis of rotation, the first axis of rotation being perpendicular to the central axis when in an initial position, the second curved inner surface and the second slide surface forming a second joint rotatable about a second axis of rotation, the second axis of rotation intersecting the central axis at an acute angle α, the second axis of rotation being spaced apart from the first axis of rotation by a distance A as measured along the central axis, wherein 0<distance A<18 mm.

2. The intervertebral implant as claimed in claim 1, wherein the first axis of rotation and the second axis of rotation cross each other.

3. The intervertebral implant as claimed in claim 1, wherein the first curved inner surface has a first radius of curvature and the first external convex slide surface has a second radius of curvature, the first radius of curvature being not equal to the second radius of curvature.

4. The intervertebral implant as claimed in claim 1, wherein at least one of the slide surfaces has a first radius of curvature and at least one of the curved inner surfaces of the terminal parts has a second radius of curvature, the first radius of curvature being not equal to the second radius of curvature.

5. The intervertebral implant as claimed in claim 1, wherein the first slide surface of the joint element is complementary to the first curved inner surface.

6. The intervertebral implant as claimed in claim 1, wherein the second slide surface of the joint element is complementary to the second curved inner surface.

7. The intervertebral implant as claimed in claim 1, wherein the angle α is between 60 and 88 degrees.

8. The intervertebral implant as claimed in claim 1, wherein the outermost surfaces exhibit a three-dimensional structure.

9. The intervertebral implant as claimed in claim 1, wherein the outermost surfaces are titanium grids that can be connected to the terminal parts.

10. The intervertebral implant as claimed in claim 1, wherein:
    at least one of the terminal parts comprises a first rotation-restricting stop shortening a front side of the intervertebral implant parallel to the central axis about the first axis of rotation at an angle of rotation γ between 5 and 15 degrees; and
    at least one of the terminal parts includes a second rotation-restricting stop shortening a rear side of the intervertebral implant parallel to the central axis about the first axis of rotation at an angle of rotation β between 2 and 15 degrees.

11. The intervertebral implant as claimed in claim 10, further comprising a third rotation-restricting stop restricting the rotation about the second axis of rotation at a maximum angle of rotation δ between −0.5 degrees and +10 degrees.

12. The intervertebral implant as claimed in claim 1, wherein at least one of the terminal parts is a three-element part and comprises an outermost cover plate, a joint pan enclosing the curved inner surface and in-between an elastically deforming spacer.

* * * * *